United States Patent [19]
Kato et al.

[11] Patent Number: 5,962,328
[45] Date of Patent: Oct. 5, 1999

[54] ELECTROLYTIC SOLUTION FORK KARL FISCHER COULOMETRIC TITRATION AND METHOD FOR WATER CONTENT DETERMINATION USING THE ELECTROLYTIC SOLUTION

[75] Inventors: Hiromasa Kato; Naoko Katayama, both of Kanagawa, Japan

[73] Assignee: Mitsubishi Chemical Corporation, Tokyo, Japan

[21] Appl. No.: 08/882,074

[22] Filed: Jun. 25, 1997

[30] Foreign Application Priority Data

Jun. 25, 1996 [JP] Japan .................................... 8-164148
May 20, 1997 [JP] Japan .................................... 9-129575

[51] Int. Cl.$^6$ .................................................. G01N 33/18
[52] U.S. Cl. ........................... 436/42; 436/166; 436/106; 436/111
[58] Field of Search ................................. 436/39, 40, 42, 436/111, 122, 163, 180, 112, 166, 106

[56] References Cited

U.S. PATENT DOCUMENTS 5,401,662 3/1995 Matschiner et al. .

FOREIGN PATENT DOCUMENTS 0 484 622 5/1992 European Pat. Off. .
2 069 148 8/1981 United Kingdom .

*Primary Examiner*—Lyle A. Alexander
*Attorney, Agent, or Firm*—Oblon, Spivak, McClelland, Maier & Neustadt, P.C.

[57] ABSTRACT

An electrolytic solution for Karl Fischer coulometric titration is disclosed which consists mainly of an amine, sulfur dioxide, iodide ions, and a solvent which is a mixed solvent comprising (a) propylene carbonate and (b) a dialkylene glycol monoalkyl ether (wherein the alkylene groups and the alkyl group each have from 1 to 4 carbon atoms). The electrolytic solution, which is based on a less toxic solvent, has fewer side reactions with ketones and is useful in accurately determining the water content of ketones.

20 Claims, No Drawings

ELECTROLYTIC SOLUTION FORK KARL FISCHER COULOMETRIC TITRATION AND METHOD FOR WATER CONTENT DETERMINATION USING THE ELECTROLYTIC SOLUTION

BACKGROUND OF THE INVENTION

1. Field of the Invention

The present invention relates to an electrolytic solution for Karl Fischer coulometric titration and to a method for determining the water content of a sample using the same. The electrolytic solution is especially suitable for use in Karl Fischer coulometric titration for determining the water contents of ketones.

2. Discussion of the Background

Karl Fischer titration is a technique for determining water based on the Karl Fischer reactions shown by the following reaction formulae.

$$I_2 + SO_2 + H_2O + 3\text{Base} \rightarrow 2(\text{Base} \cdot HI) + \text{Base} \cdot SO_3 \quad (1)$$

$$\text{Base} \cdot SO_3 + CH_3OH \rightarrow \text{Base} \cdot H^+ + CH_3OSO_3^- \quad (2)$$

[In formulae (1) and (2), "Base" represents a basic compound.]

Techniques for determining water based on the Karl Fischer reactions are classified into volumetric titration and coulometric titration. The present invention relates to coulometric titration. In coulometric titration methods, the iodine on the left side of the reaction formula (1) is generated from iodide ions supplied to the electrolytic solution by oxidizing the iodide ions at the anode as shown by the following formula (3).

$$2I^- \rightarrow I_2 + 2e \quad (3)$$

In coulometric titration, the amount of iodine used in the reaction shown by formula (1) is calculated from the quantity of electricity required for the oxidation reaction. The water content of the sample is calculated from the amount of iodine.

The reaction shown by formula (1) is an equilibrium reaction. When a lower alcohol such as methanol is present, the reaction shown by formula (2) proceeds and, as a result, the equilibrium of the reaction shown by formula (1) shifts to the right to complete the Karl Fischer reactions. Hence, all the electrolytic solutions which have ordinarily been used for coulometric titration contain a lower alcohol such as methanol. However, in the case where a ketone such as acetone or cyclohexanone is used as a sample to determine the water content thereof, the ketone reacts with methanol (ketal reaction) to yield water, which is indistinguishable from the water originally contained in the ketone and thus makes accurate measurement impossible. It is therefore necessary to use an electrolytic solution in which the solvent does not contain any lower alcohol such as methanol.

Consequently, previous determination of the water content of ketone samples has been conducted using an electrolytic solution for coulometric titration containing chloroform or methyl Cellosolve as a solvent (see, for example, JP-B-62-16378 and JP-B-5-27063). (The term "JP-B" as used herein means an "examined Japanese patent publication".)

Recently, however, animal experiments revealed that chloroform is carcinogenic, and it has been pointed out that methyl Cellosolve (ethylene glycol monomethyl ether) is toxic to the testes. Therefore, the use of these solvents should be avoided.

JP-A-5-10923 (U.S. Pat. No. 5,187,101) discloses using a lower aliphatic alcohol, e.g., methanol, a propylene glycol mono(lower alkyl) ether, etc. as a solvent in an electrolytic solution for Karl Fischer coulometric titration. (The term "JP-A" as used herein means an "unexamined published Japanese patent application".) Also described is that a mixed solvent containing propylene carbonate or another compound is usable.

However, the invention disclosed in JP-A-5-10923 is not intended for use in determining the water content of a ketone, and all the Examples given therein use a solvent consisting mainly of methanol. Even when a mixed solvent consisting of a propylene glycol mono(lower alkyl) ether and propylene carbonate was used for determining the amount of water which was 10 $\mu l$, the found value was 9,081 $\mu g$, as shown in a Comparative Example given later. The above mixed solvent is hence unsatisfactory in accuracy.

In ordinary moisture meters for coulometric titration, a small electrolytic current is always flowing between the anode and cathode within the titration cell, even before the initiation of the measurement (anhydrous state). When water enters the titration cell, that electrolytic current increases, and the oxidation of iodide ions at the anode occurs. The electrolytic current continuously flows until all the water is consumed in the Karl Fischer reactions. At the time when the electrolytic current has decreased to or below a given value, the measurement is terminated. The value of the electrolytic current in a titration cell in an anhydrous state is referred to as the "background value". (According to ordinary practice, the "value of electrolytic current" is usually converted to "the rate of iodine generation", which in turn is converted to the amount of $H_2O$ titrated per second ($\mu g \cdot H_2O$/sec).)

If an electrolytic solution is used for analyzing a ketone sample with a moisture meter for Karl Fischer coulometric titration and the moisture meter shows a low background value (close to 0), then the low background value means that the components of the electrolytic solution undergo no side reactions with the ketone or undergo side reactions which produce little effect. In this case, the electrolytic solution can be regarded as suitable for the analysis of the ketone. On the other hand, if the moisture meter shows a high background value, this means that the electrolytic solution is undergoing side reactions. In this case, an accurate measurement is impossible and the electrolytic solution is therefore unsuitable for the analysis.

SUMMARY OF THE INVENTION

An object of the present invention is to provide an electrolytic solution which is based on a less toxic solvent and does not contain methanol, and therefore undergoes fewer side reactions, even in the determination of the water content of a ketone.

As a result of intensive studies made by the present inventors, they have discovered an electrolytic solution which is suitable for the determination of the water content of a ketone, such as acetone or cyclohexanone, and does not contain any harmful solvent, such as chloroform or methyl Cellosolve. They have further discovered a method for water content determination using the electrolytic solution.

The present invention provides an electrolytic solution for Karl Fischer coulometric titration containing mainly an amine, sulfur dioxide, iodide ions, and a solvent which is a mixed solvent comprising (a) propylene carbonate and (b) a dialkylene glycol monoalkyl ether (wherein the alkylene groups and the alkyl group each has from 1 to 4 carbon atoms). The present invention further provides a method for coulometrically determining the water content of a sample using the electrolytic solution.

DETAILED DESCRIPTION OF THE INVENTION

Solvents (a) and (b) for use in the present invention are safe. There has been no report which points out that either of these is toxic.

Propylene carbonate, used as solvent (a) in the present invention, does not react with ketones and has a high permittivity. Since this solvent reduces the resistance of an electrolytic solution, it brings about a higher efficiency of electrolytic current and enables titration to be conducted smoothly and accurately. Thus, this solvent is suitable for use in an electrolytic solution for Karl Fischer coulometric titration.

On the other hand, a solvent which has an OH group similar to that of methanol and is capable of dissociating to release $H^+$ is appropriate for an electrolytic solution for Karl Fischer coulometric titration, because this solvent serves to allow the Karl Fischer reaction shown by formula (1) to proceed to the right. The dialkylene glycol monoalkyl ether (wherein the alkylene groups and the alkyl group each have 1 to 4 carbon atoms) used as solvent (b) in the present invention contains an OH group, but has less tendency to dissociate and release the OH group. Solvent (b) is therefore slowly reactive with ketones, and generates only a slight amount of water through a ketal reaction. The water generated is negligible in the determination of the water content.

Whether a ketal reaction takes place or not can be judged based on measurement of the "background value". The reason for this is as follows. The water contained in a sample is rapidly consumed by the Karl Fischer (KF) reactions, and the "background value" also should drop rapidly if no water is being generated in the sample. On the other hand, a ketal reaction proceeds slowly to gradually yield water, so that the background value does not readily decrease. Based on these ways in which the background value may change, the occurrence or nonoccurrence of a ketal reaction can be gauged from the background. In other words, by following the background value, the degree of the ketal reaction which the solvent system is undergoing can be found. It is therefore necessary to select a solvent which not only gives an accurate determination but also gives a low "background value" after ketone analysis.

Examples of the dialkylene glycol monoalkyl ether (b) used in the present invention include diethylene glycol monoalkyl ethers and dipropyl glycol monoalkyl ethers. (In these ethers, the alkyl group represents methyl, ethyl, propyl, or butyl.) Preferred among these are diethylene glycol monoethyl ether and diethylene glycol monobutyl ether. In particular, diethylene glycol monoethyl ether is especially preferred.

In the present invention, a mixture of solvents (a) and (b) is preferably used. This mixed solvent provides an electrolytic solution for Karl Fischer coulometric titration which enables the Karl Fischer reactions to proceed normally and undergoes almost no ketal reaction, and in which reactants for the Karl Fischer reactions are soluble in a sufficient amount.

The solvents (a) and (b) are mixed with each other in a volume ratio of generally from 1:9 to 9:1, preferably from 3:7 to 7:3.

Preferably any amine having an acid dissociation constant $pK_a$ of 5 or higher may be used in the present invention. Those having a $pK_a$ of 6 or higher are more desirable. Preferred examples of the amine include pyridine derivatives such as 1,3-di(2-pyridyl)propane, 1,3-di(4-pyridyl) propane, 2-methylaminopyridine, and 4-dimethylaminopyridine. These pyridine derivatives may be used alone or as a mixture thereof. Especially preferred is a mixture of 1,3-di(4-pyridyl)propane and 4-dimethylaminopyridine. Other usable amines include imidazole, derivatives thereof (e.g., 1-methylimidazole, 2-ethylimidazole, and 2-phenylimidazole), guanidine benzoate, and the like. The amine concentration is preferably from 0.1 to 3 M (mol/l; the same applies hereinafter), more preferably from 0.3 to 1 M.

The concentration of sulfur dioxide is preferably from 0.1 to 3 M, more preferably from 0.3 to 1.5 M. In the case where 4-dimethylaminopyridine is used alone as the amine, sulfur dioxide should be used in a higher concentration than the 4-dimethylaminopyridine, because of the high basicity of the amine.

The concentration of iodide ions is preferably from 0.03 to 2 M, more preferably from 0.1 to 1.0 M.

Each component of the electrolytic solution may free or in chemical association. Chemical association includes solvated, complexed, or otherwise interacting with other components.

The electrolytic solution of the present invention is used in a known apparatus for Karl Fischer coulometric titration which comprises an anode chamber having an anode, a cathode chamber having a cathode, and a diaphragm, e.g., a sintered glass, ceramic, or ion-exchange membrane, which separates the two chambers from each other. The electrolytic solution of the invention is used as an anolyte (electrolyte in contact with the anode) in the anode chamber. A known catholyte (electrolyte in contact with the cathode) may be used without any particular limitation, as long as it is a non-aqueous electrolyte solution which has conductivity sufficient to permit a desired electrolytic current to flow therethrough, and which does not contain any oxidizing or reducing substance which would inhibit the Karl Fischer reactions, nor generates inhibitory substance through an electrode reaction. Specifically, a solution of an electrolyte (conductive salt) in a non-aqueous solvent may be used as the catholyte. Examples of the electrolyte include organic salts such as salts of at least one member selected from the group consisting of amines and guanidine with a halogenated hydroacid, nitric acid, or perchloric acid (e.g., diethanolamine); quaternary compounds (e.g., tetramethylammonium chloride, tetraethylammonium chloride, and choline chloride); and inorganic salts, such as salts of ammonia, an alkali metal, or an alkaline earth metal with a halogenated hydroacid, nitric acid, or perchloric acid (e.g., lithium chloride). Examples of the non-aqueous solvent include lower alcohols having 1 to 4 carbon atoms, such as methanol, ethanol, and propanol, and lower alkylene glycols such as ethylene glycol. These solvents may be used alone or as a mixture of two or more thereof. Preferred is a mixed solvent consisting of methanol and ethylene glycol. The electrolyte concentration in the catholyte is from 0.01 to 10 mol/l, preferably from 0.5 to 5 mol/l.

The present invention will be explained below in more detail by reference to Examples. However, the invention should not be construed as being limited to the following Examples.

EXAMPLE 1

In a mixture of 100 ml of propylene carbonate and 90 ml of diethylene glycol monoethyl ether were dissolved 36 g of 1,3-di(4-pyridyl)propane and 12 g of sulfur dioxide. Thereto was added 8 g of iodine. Propylene carbonate containing 0.5 ml of pure water was further added to adjust the total volume to 300 ml. This solution was used as an anolyte. A solution prepared by mixing choline chloride with methanol and ethylene glycol in a weight ratio of 1:1:1 was used as a catholyte. The electrolytic cells of commercial coulometric moisture meter Model CA-06 (trade name; product of Mitsubishi Chemical Corp., Japan) were respectively filled with the anolyte and catholyte prepared above. The inside of each electrolytic cell was brought into an anhydrous state according to the instruction manual.

First, the apparatus was examined for accuracy through the determination of 10 μl of water. As a result, values exceedingly close to the theoretical value of 10,000 μg were obtained. Thereafter, 1 ml of acetone was injected into an electrolytic cell to measure the water content thereof. This operation was repeated ten times. The background value after the first measurement was 0.06 μg/sec, which was sufficiently low, indicating that almost no side reactions occurred. Throughout the subsequent measurements, little increase in background value was observed. Even after the tenth measurement, the resultant background value was only higher than that for the preceding measurement by a value far lower than 0.1 μg/sec. Namely, the system was capable of being used for further measurements. The results of the above measurements are shown in Table 1. (In each measurement with that apparatus, the titration was terminated at the time when the found value of electrolytic current decreased to or below a value higher by 0.1 μg/sec than the background value after the preceding measurement.)

EXAMPLE 2

The same procedure as in Example 1 was conducted, except that 21 g of 1,3-di(4-pyridyl)propane and 18 g of 4-dimethylaminopyridine were used in place of 36 g of 1,3-di(4-pyridyl)propane. The results obtained are shown in Table 1.

Comparative Example 1

The same procedure as in Example 1 was conducted, except that methanol was used in place of propylene carbonate. The results obtained are shown in Table 1.

Comparative Example 2

The same procedure as in Example 1 was conducted, except that methanol was used in place of diethylene glycol monomethyl ether. The results obtained are shown in Table 1.

TABLE 1

| | Example 1 | | Example 2 | | Comparative Example 1 | Comparative Example 2 |
|---|---|---|---|---|---|---|
| Water, 10 μl | 9849 μg | | 9884 μg | | 9945 μg | 9953 μg |
| Acetone 1 ml for each measurement | Found value | Background | Found value | Background | | |
| 1 | 1800 μg | 0.06 μg/sec | 1761 μg | 0.04 μg/sec | Measurement was impoasible because the background value after the first acetone analysis was higher than 1 μg/sec. | |
| 2 | 1797 | 0.13 | 1791 | 0.06 | | |
| 3 | 1800 | 0.18 | 1750 | 0.09 | | |
| 4 | 1817 | 0.23 | 1760 | 0.11 | | |
| 5 | 1824 | 0.26 | 1769 | 0.11 | | |
| 6 | 1807 | 0.26 | 1777 | 0.14 | | |
| 7 | 1802 | 0.33 | 1735 | 0.15 | | |
| 8 | 1812 | 0.37 | 1728 | 0.15 | | |
| 9 | 1819 | 0.40 | 1742 | 0.17 | | |
| 10 | 1811 | 0.43 | 1738 | 0.20 | | |
| Average | 1809 μg | | 1755 μg | | | |
| Coefficient of variation | 0.50% | | 1.1% | | | |

$$\text{Coefficient of variation} = \frac{\sqrt{\frac{\sum_{i=1}^{n}(X_i - \bar{x})^2}{(n-1)}}}{\bar{x}} \times 100$$

$\bar{x}$: average
$X_i$: found value in the first measurement
$n$: number of measurements

EXAMPLE 3

In a mixture of 100 ml of propylene carbonate and 150 ml of diethylene glycol monoethyl ether were dissolved 12.2 g of imidazole and 5.8 g of sulfur dioxide. Thereto was added 3.8 g of iodine. Propylene carbonate was further added to adjust the total volume to 300 ml. This solution was used as an anolyte. The subsequent procedure was conducted in the same manner as in Example 1, except that 100 ml of the solution prepared above was used. The results obtained are shown in Table 2.

TABLE 2

| | Example 3 | |
|---|---|---|
| Water, 10 μl | 9878 μg | |
| Acetone, 1 ml for each measurement | Found value | Background |
| 1 | 1463 μg | 0.10 |
| 2 | 1482 | 0.17 |
| 3 | 1463 | 0.22 |
| 4 | 1463 | 0.26 |

TABLE 2-continued

| | Example 3 | |
|---|---|---|
| 5 | 1466 | 0.32 |
| 6 | 1472 | 0.34 |
| 7 | 1461 | 0.33 |
| 8 | 1463 | 0.38 |
| 9 | 1464 | 0.42 |
| 10 | 1460 | 0.43 |
| Average | | 1466 μg |
| Coefficient of variation | | 0.44% |

Comparative Example 3

Anolyte preparation was attempted in the same manner as in Example 2, except that propylene carbonate was used in place of diethylene glycol monoethyl ether. As a result, a precipitate generated during the preparation, and the resultant liquid was unable to be used as an anolyte.

Comparative Example 4

In a mixture of 100 ml of propylene carbonate and 90 ml of propylene glycol monomethyl ether were dissolved 39 g of 2-methylaminopyridine and 12 g of sulfur dioxide. Thereto was added 8 g of iodine. Propylene carbonate was further added to adjust the total volume to 300 ml. This solution was used as an anolyte to determine 10 μl of water in the same manner as in Example 1. As a result, the found value was 9,081.6 μg (average for three measurements; coefficient of variation, 1.0%), showing that the measurements had poor accuracy.

By the use of the electrolytic solution for Karl Fischer coulometric titration of the present invention, ketones can be analyzed to determine the water contained therein in a slight amount, without using any harmful solvent such as chloroform or methyl Cellosolve.

While the invention has been described in detail and with reference to specific embodiments thereof, it will be apparent to one skilled in the art that various changes and modifications can be made therein without departing from the spirit and scope thereof.

The priority documents of the present invention, Hei. 8-164148 and Hei. 9-129575, filed in Japan on Jun. 25, 1996 and May 20, 1997, respectively, are hereby incorporated by reference.

What is claimed is:

1. An electrolytic solution for Karl Fischer coulometric titration comprising an amine, sulfur dioxide, iodide ions and a solvent free or in chemical association,
    wherein the solvent comprises (a) propylene carbonate and (b) a dialkylene glycol monoalkyl ether, in which the alkylene groups and the alkyl group each have from 1 to 4 carbon atoms.

2. The electrolytic solution of claim 1, wherein the solvent comprises (a) and (b) in a volume ratio of from 1:9 to 9:1.

3. The electrolytic solution of claim 1, wherein the amine has an acid dissociation constant $pK_a$ of at least 5.

4. The electrolytic solution of claim 1, wherein the amine is at least one member selected from the group consisting of 1,3-di(2-pyridyl)propane, 1,3-di(4-pyridyl)propane, 2-methylaminopyridine, 4-dimethylaminopyridine and imidazole.

5. The electrolytic solution of claim 2, wherein the solvent comprises (a) and (b) in a volume ratio of from 3:7 to 7:3.

6. The electrolytic solution of claim 3, wherein the amine has an acid dissociation constant $pK_a$ of at least 6.

7. The electrolytic solution of claim 1, wherein said dialkylene glycol monoalkyl ether is selected from the group consisting of diethylene glycol monoethyl ether, diethylene glycol monobutyl ether and mixtures thereof.

8. The electrolytic solution of claim 1, wherein said solution does not contain methanol.

9. The electrolytic solution of claim 1, wherein said solution consists essentially of said amine, said sulfur dioxide, said iodide ions and said solvent.

10. An electrolytic solution for Karl Fischer coulometric titration, prepared by mixing an amine, sulfur dioxide, iodide ions, propylene carbonate and a dialkylene glycol monoalkyl ether, in which the alkylene groups and the alkyl groups each have from 1 to 4 carbon atoms.

11. The electrolytic solution of claim 10, wherein said propylene carbonate and said dialkylene glycol monoalkyl ether are present in a volume ratio of from 1:9 to 9:1.

12. The electrolytic solution of claim 10, wherein the amine has an acid dissociation constant $pK_a$ of at least 5.

13. The electrolytic solution of claim 10, wherein the amine is at least one member selected from the group consisting of 1,3-di(2-pyridyl)propane, 1,3-di(4-pyridyl)propane, 2-methylaminopyridine, 4-dimethylaminopyridine and imidazole.

14. The electrolytic solution of claim 11, wherein said propylene carbonate and said dialkylene glycol monoalkyl ether are present in a volume ratio of from 3:7 to 7:3.

15. The electrolytic solution of claim 12, wherein the amine has an acid dissociation constant $pK_a$ of at least 6.

16. The electrolytic solution of claim 10, wherein said dialkylene glycol monoalkyl ether is selected from the group consisting of diethylene glycol monoethyl ether, diethylene glycol monobutyl ether and mixtures thereof.

17. The electrolytic solution of claim 10, wherein said solution does not contain methanol.

18. An process for preparing the electrolytic solution of claim 10, comprising mixing said amine, said sulfur dioxide, said iodide ions, said propylene carbonate and said dialkylene glycol monoalkyl ether.

19. A method for coulometrically determining the water content of a sample, comprising performing a Karl Fischer coulometric titration, wherein said titration is carried out in a solvent comprising (a) propylene carbonate and (b) a dialkylene glycol monoalkyl ether, in which the alkylene groups and the alkyl group each have from 1 to 4 carbon atoms.

20. The method of claim 19, wherein the sample comprises a ketone.

* * * * *

UNITED STATES PATENT AND TRADEMARK OFFICE
CERTIFICATE OF CORRECTION

PATENT NO. : 5,962,328

DATED : October 5, 1999

INVENTOR(S): Hiromasa KATO et al.

It is certified that an error appears in the above-identified patent and that said Letters Patent is hereby corrected as shown below:

On the title page, item [54], and at the top of Column 1, the title should be:

--ELECTROLYTIC SOLUTION FOR KARL FISCHER COULOMETRIC TITRATION AND METHOD FOR WATER CONTENT DETERMINATION USING THE ELECTROLYTIC SOLUTION--

Signed and Sealed this

Twenty-seventh Day of February, 2001

*Attest:*

NICHOLAS P. GODICI

*Attesting Officer*   *Acting Director of the United States Patent and Trademark Office*